(12) United States Patent
Okada

(10) Patent No.: US 6,186,148 B1
(45) Date of Patent: Feb. 13, 2001

(54) PREVENTION OF POSTERIOR CAPSULAR OPACIFICATION

(76) Inventor: Kiyoshi Okada, 30-304, Ichigaya Yakuoji-cho, Shinjuku-ku, Tokyo 162-0063 (JP)

(*) Notice: Under 35 U.S.C. 154(b), the term of this patent shall be extended for 0 days.

(21) Appl. No.: 09/373,183

(22) Filed: Aug. 12, 1999

Related U.S. Application Data

(63) Continuation of application No. 09/368,786, filed on Aug. 5, 1999, now abandoned, which is a continuation-in-part of application No. 09/017,716, filed on Feb. 4, 1998.

(51) Int. Cl.$^7$ ............................................. A61B 19/00
(52) U.S. Cl. ........................................ 128/898; 623/6.56
(58) Field of Search .......................... 128/898; 623/4.1, 623/6.11, 6.56; 435/183; 514/2

(56) References Cited

U.S. PATENT DOCUMENTS

| | | |
|---|---|---|
| Re. 31,626 | 7/1984 | Hoffer . |
| 4,412,359 | 11/1983 | Myers . |
| 4,485,499 | 12/1984 | Castleman . |
| 4,642,114 | 2/1987 | Rosa . |
| 4,655,775 | 4/1987 | Clasby, III . |
| 4,725,276 | 2/1988 | Bissonette et al. . |
| 4,738,680 | 4/1988 | Herman . |
| 4,764,169 | 8/1988 | Grendahl . |
| 5,041,135 | 8/1991 | Charleux . |
| 5,275,624 | 1/1994 | Hara et al. . |
| 5,366,501 | 11/1994 | Langerman . |
| 5,370,687 | 12/1994 | Poler . |
| 5,376,116 | 12/1994 | Poler . |
| 5,593,436 | 1/1997 | Langerman . |
| 5,618,553 | 4/1997 | Kelleher . |
| 5,843,184 | 12/1998 | Cionni . |

OTHER PUBLICATIONS

Christopher P. Born, M.D. et al., Effect of intraocular lens optic design on posterior capsular opacification, *J Cataract Refract Surg*, vol. 16, Mar. 1990, pp. 188–192.

R. Bougaran et al., A Capsular Ring to Prevent Complications After Cataract Surgery, *Investigative Ophthalmology & Visual Science*, vol. 38, No. 4, Mar. 15, 1997, p. S144.

David A. Hiles et al., Modern Intraocular lens implants in children with new age limitations, *J. Cataract Refract Surg*, vol. 13, Sep. 1987, pp. 493–497.

Barry A. Maltzman, M.D. et al., Effect of the laser ridge on posterior capsule opacification. *J. Cataract Refract Surg*, vol. 15, Nov. 1989, pp. 644–646.

T. Nagamoto et al., Prevention of Secondary Cataract by Blocking Capsular Adhesion with a Newly Designed Intraocular Lens, *IOVS*, vol. 40, No. 4, Mar. 15, 1999, p. S295.

Toyofumi Nagata et al., Optic Sharp Edge or Convexity: Comparison of Effects on Posterior Capsular Opacification, *Jpn J Ophthalmol*, vol. 40, 1996, pp. 397–403.

Okihiro Nishi, M.D. et al., Inhibition of Migrating Lens Epithelial Cells at the Capsular Bend Created by the Rectangular Optic Edge of a Posterior Chamber Intraocular Lens, *Opthalmic Surgery and Lasers*, vol. 29, No. 7, Jul. 1998, pp. 587–594.

Tetsuro Oshika, M.D. et al., Two year clinical study of a soft acrylic intraocular lens, *J. Cataract Refract Surg*, vol. 22, Jan./Feb. 1996, pp. 104–109.

Keiko Yamada, M.D., et al., Effect of intraocular lens design on posterior capsule opacification after continuous curvilinear capsulorhexis, *J. Cataract Refract Surg*, vol. 21, Nov. 1995, pp. 697–700.

Morcher—Special Implants, www.morcher.com/produkte/sonder/engl/e_sonder.htm, Sep. 17, 1999, pp. 1–4.

Beatrice Cochener, M.D. et al., Secondary cataract inhibition by a capsular ring–bound sustained drug delivery system, *Best papers from the 1998 ASCRS meeting*, p. 7.

Sean Charles, PCO Delayed in Paediatric Cataract Patients With Foldable Acrylic IOL, *Cataract & Refractive Surgery Euro Times*, May–Jun. 1999, p. 10.

*Primary Examiner*—Dinh X. Nguyen
(74) *Attorney, Agent, or Firm*—Knobbe, Martens, Olson & Bear, LLP

(57) ABSTRACT

Posterior capsular opacification can be prevented by modulating focal contacts, which mediate adhesion between lens epithelial cells and the lens capsule, using a treating solution containing a focal contact-modulating substance or a proenzyme, such as Lys-plasminogen, which is introduced into the lens capsular bag during cataract surgery. To secure the passage of a treating solution between the lens epithelial cells, a calcium chelating agent, such as ethylenediamine tetraacetic acid CEDTA), is included in a treating solution. To limit the effect of the treating solution to lens epithelial cells prior to, during, and/or after capsulotomy, an inhibitor, such as ω-amino acid, can be introduced into the anterior chamber before the treating solution as a mixture with a viscoelastic material, such as sodium hyaluronate, or into the lens capsular bag without a viscoelastic material during capsulotomy.

22 Claims, No Drawings

PREVENTION OF POSTERIOR CAPSULAR OPACIFICATION

RELATED APPLICATION

This is a continuation of application Ser. No. 09/368,786, filed Aug. 5, 1999, now abandoned, which is a continuation-in-part application of application Ser. No 09/017,716, filed on Feb. 4, 1998.

BACKGROUND OF THE INVENTION

1. Field of the Invention

The present invention relates to cataract surgery, specifically to compositions and methods for preventing proliferation of remnant lens epithelial cells occurring after cataract surgery. More specifically, the invention relates to the use of a combination for prevention of posterior capular opacification, particularly for surgically difficult cases.

2. Background of the Art

A natural lens is enveloped in a structure called the lens capsule, which is the basement membrane of lens epithelial cells, and held behind the iris and in front of the vitreous by a suspensory ligament called the zonules. The inside of the lens capsule consists of lens epithelial cells and lens fibers. Lens epithelial cells form a monolayer underlying the lens capsule from the anterior pole to the equator of the lens. Lens fibers occupy the rest of the inside of the lens capsule. Lens epithelial cells become elongated in the equator of the lens and turn into lens fibers. As well as the morphological change, lens epithelial cells show the alteration in biochemical features. That is, protein synthesis of lens epithelial cells greatly changes toward the lens equator. These morphological and biochemical changes are called differentiation. In an area between the anterior pole and the lens equator, lens epithelial cells continue to undergo cell mitosis throughout life. This area is called germinate zone. Lens epithelial cells that underwent cell mitosis in the germinate zone gradually move toward the lens equator and differentiate into lens fibers.

Lens fibers are divided into two parts; the lens cortex and the lens nucleus. The lens cortex is a relatively soft tissue that consists of young lens fibers located near the lens equator. These fibers accumulate throughout life and gradually lose their intracellular organelles moving toward the center of the lens forming a hard, closely packed lamellar structure called the lens nucleus.

In the prevailing cataract surgical procedure, i.e., extra-capsular cataract extraction, an incision is made in the anterior part of the eye, i.e., the cornea, the sclera or the corneal scleral junction. A viscoelastic material is then introduced into the anterior chamber to maintain the anterior chamber depth. An opening is then made in the lens capsule. This procedure is called capsulotomy or capsulorhexis. Following capsulotomy, the clouded lens nucleus and lens cortex, mainly the lens nucleus, are fragmented by phacoemulsification and taken out of the eye, or simply delivered through the lens capsular opening when the nucleus is too hard to be fragmented. The lens cortex is then removed by using an irrigation and aspiration device while the anterior chamber and the lens capsular bag are irrigated with a physiological solution. If applicable, an intraocular lens (artificial lens) is inserted inside the remaining lens capsular bag after the lens capsular bag, is filled with a viscoelastic material. The term "lens capsular bag" means, herein, the lens capsule in which at least one opening or one hole is made. In the prevailing cataract surgical procedure, lens epithelial cells cannot be separated from the lens capsule so that postoperatively the remnant lens epithelial cells on the lens capsule proliferate and/or migrate toward the center on the posterior lens capsule. Due to the proliferated lens epithelial cells, the residual lens capsule becomes opacified, which obstructs the visual axis and causes a visual disturbance. This is called posterior capsular opacification or secondary cataract. The primary object of the present invention is to develop compositions and methods to prevent the proliferation of remnant lens epithelial cells following cataract surgery.

More than 1.3 million cataract surgeries are performed in the United States annually. Of patients who undergo cataract surgery, between the 20 and 40% develop posterior capsular opacification within 34 years postoperatively (Cataract Management Guideline Panel, *Ophthalmology*, 100 Suppl., 52s–55s, 273s–286s, 1993). In the current clinical standard, patients who develop posterior capsular opacification are treated by YAG laser capsulotomy. In this procedure the opacified residual lens capsule is disrupted by a YAG laser and the visual axis is cleared. However, YAG laser capsulotomy exposes patients to the risk of complications that can lead to severe visual impairment or loss of vision, such as retinal detachment, pupillary block glaucoma and cystoid macular edema (Cataract Management Guideline Panel 1993). Other complications associated with YAG laser capsulotomy include damage to implanted intraocular lenses resulting in glare and photophobia, dislocation of intraocular lenses, iritis, vitritis, corneal edema, iris damage and rupture of the anterior hyaloid face (Cataract Management Guideline Panel 1993). From an economic point of view, development of a procedure to prevent posterior capsular opacification reduces the medical costs related to YAG laser capsulotomy, including the costs for the treatment, its complications, and YAG laser equipment.

Accordingly, there is a great need for a way to prevent posterior capsular opacification.

There are mainly two approaches to prevent posterior capsular opacification; surgical and pharmacological approaches. As surgical approach, use of various surgical instruments and the application of laser, ultrasound and/or freezing techniques have been tried to separate and/or destroy the lens epithelial cells that remain attached to the lens, capsule. These attempts have turned out to be of little or no success.

As pharmacological approach, a variety of agents have been applied to destroy, kill, or separate the lens epithelial cells. However, most of these agents were not working) specific to the lens epithelial cells and, when an agent was used at an appropriate concentration to kill or destroy the lens epithelial cells, other surrounding eye tissues were damaged. In this regard, the use of a toxin-conjugated antibody against lens epithelial cells, i.e., immunotoxin, is a real possibility to specifically destroy the lens epithelial cells and prevent posterior capsular opacification. A recent clinical study indicates that the application of a ricin-conjugated antibody reduced the incidence of posterior capsular opacification but prevention of opacification was not complete (Ocular Surgery News, November 1, page 58, 1996).

Another pharmacological approach is to separate lens epithelial cells from the lens capsule. Ethylenediamine tetraacetic acid (EDTA) was included in an irrigative solution and a simulated extracapsular cataract extraction was performed to separate lens epithelial cells (Humphry et al., *Br. J. Ophthalmol.*, 72:406–8, 1988). In other attempts, EDTA was used with a viscoelastic material (U.S. Pat. No. 5,204, 331 to Nishi et al., 1993; Nishi et al., *J. Cataract Refract Surg.*, 19:56–61, 1993), or simply introduced into the lens capsular bag (Wee et al., *Invest. Ophthalmol. Vis. Sci.*, 34:887, 1993). When an EDTA solution was included in an irrigative solution and a simulated extracapsular cataract extraction was performed in cadaver eyes, the anterior lens epithelial cells could be separated (Humphry et al., 1988).

Enzymes such as trypsin (Humphry et al., 1988) and DISPASE® (Protease) (Nishi et al., *Dev. Ophthalmol.*, 22:101–105, 1991a, *Ophthalmic Surg.*, 22:444–50, 1991b) were also used to separate lens epithelial cells. When a 2% trypsin solution was included in an irrigative solution and a simulated extracapsular cataract extraction was performed in cadaver eyes, lens epithelial cells had been stripped in places. The cell separation was partially successful. Indeed, the zonules were damaged by the trypsin solution (Humphry et al., 1988). The use of an active enzyme can be a problem even when an enzyme solution is introduced into the lens capsular bag because an active enzyme can damage the zonules where the zonules are located in the lens capsule. A substantial problem in using an active enzyme was that the enzyme damaged a tissue or cells where a treating solution had contact.

According to U.S. Pat. No. 4,909,784 to Dubroff 1990, when a cell-killing substance is introduced into the lens capsule through a small hole, lens epithelial cells are killed. A viscoelastic material that is introduced into the anterior chamber prevents any of the substance escaping from the lens capsule and prevents damage to the corneal endothelium. In related patents (U.S. Pat. No. 4,909,784 to Dubroff 1990, U.S. Pat. No. 5,013,295 to Dubroff 1991), a syringe to remove the introduced substance from the lens capsule through a small hole was disclosed. However, physically and technically, it is difficult to efficiently remove the substance introduced into the lens capsular bag before capsulotomy without damaging the lens capsule. Therefore, the remaining substance can escape from the lens capsular bag and damage the cells and tissues facing the anterior chamber during and after capsulotomy. Thus, there is a great need for a way to prevent damage to cells and tissues during and after capsulotomy.

Surgically difficult cases

One of the most frequent complications in the prevailing cataract surgery is the proliferation of lens epithelial cells following cataract surgery. Lens epithelial cells that remain in the lens capsular bag at the end of the surgery proliferate on the posterior lens capsule and obstruct the visual axis postoperatively. It is called posterior capsular opacification or secondary cataract. It causes visual disturbance or glare. When an eye develops posterior capsular opacification, the patient is treated by YAG laser capsulotomy. However, the YAG laser treatment exposes patients to the risk of severe visual impairment or loss of vision to develop retinal detachment, glaucoma and cystoid macula edema. Accordingly, there is a great need to develop a method and a composition to prevent posterior capsular opacification.

It has been reported that the incidence of YAG laser capsulotomy can be reduced by implanting an intraocular lens (IOL) with truncated sharp optic edges such as AcrySof® IOLs (Alcon Lab.) and CeeOn® silicone IOLs (Pharmacia & Upjohn Inc.). However, according to the clinical trials of these IOLs, still YAG laser capsulotomy is required in 10% or more of patients who undergo cataract surgery (Oshika et al., J Cataract Refract Surg. 22:104–109, 1998.). In pediatric cases with implantation of AcrySof® IOLs, 25% of patients require YAG laser capsulotomy (Cataract & Refractive Surgery, Euro Times, May–June 1999, p10). It was recently suggested that development of posterior capsular opacification would be reduced by implanting a convex-plano (plano-posterior) IOL in eyes in which continuous circular (or curvilinear) capsulorhexis was performed (Yamada et al., J Cataract Refract Surg. 21:697–700,1995. Nagata et al., Jpn J Ophthalmol. 40:397–403,1996.). Other devices and IOLs to prevent posterior capsular opacification, e.g., capsular ring, have been developed. However, the efficacy of the devices and the IOLs has not yet been established or the clinical outcome was not successful (Born et al., J Cataract Refract Surg. 16:188–192,1990. Maltzman et al., J Cataract Refract Surg. 15:644–646,1989.). Accordingly, elimination of YAG laser capsulotomy is not achieved by simply implanting an IOL with the truncated optic design or other devices and IOLs. For prevention of posterior capsular opacification, compositions and methods were disclosed by the present inventor in U.S. patent application Ser. No. 09/017,716. The disclosed methods substantially successfully prevent posterior capsular opacification. However, there can be some difficult surgical conditions and challenging cases that may result in incomplete removal or separation of lens epithelial cells. In order to eliminate YAG laser capsulotomy, inhibition of posterior capsular opacification has to be secured in any patient. Approximately 3.7 million cataract surgeries are performed annually worldwide and patients who develop posterior capsular opacification due to incomplete removal or separation of lens epithelial cells cannot be ignored. It is because, unless elimination of YAG laser capsulotomy is achieved, expensive YAG laser equipment has to be reserved for the back-up treatment. This aspect has not been seriously considered in the literature. The present invention provides the improved methods for prevention of posterior capsular opacification to eliminate YAG laser capsulotomy. The methods are effective in surgically difficult situations and cases and challenging cases.

SUMMARY OF THE INVENTION

The present invention has exploited cataract surgery, especially prevention of subsequent proliferation of remnant lens epithelial cells. An objective of the present invention is to provide compositions and methods for preventing proliferation of remnant lens epithelial cells following cataract surgery. For this purpose, in the present invention, upon elucidation of the localization of structures that mediate the adhesion between lens epithelial cells and the lens capsule, the present invention provides compositions and methods for separating lens epithelial cells from the lens capsule. Namely, one important aspect of the present invention is a pharmaceutical composition for separating lens epithelial cells and preventing posterior capsular opacification, comprising: a focal contact-modulating substance or a proenzyme for mediating adhesion between lens epithelial cells and the lens capsule, said focal contact-modulating substance capable of modulating focal contacts to release the adhesion between said lens epithelial cells and the lens capsule, in an effective amount; and a pharmaceutically acceptable carrier. By attacking focal contacts, which mediate adhesion between lens epithelial cells and the lens capsule, using a focal contact-modulating substance or a proenzyme, the interface between lens epithelial cells and the lens capsule can be separated with minimized damage to other cells.

In brief, according to the present invention, posterior capsular opacification can be prevented by modulating focal contacts, using a treating solution containing a focal contact-modulating substance or a proenzyme, which is introduced into the lens capsular bag during cataract surgery. To secure the passage of a treating solution between the leas epithelial cells, a calcium chelating agent may be included in a treating solution. To limit the effect of the treating solution to lens epithelial cells prior to, during, and/or after capsulotomy, an inhibitor can be introduced into the anterior chamber as a mixture wink a viscoelastic material before the introduction of the treating solution and/or into the lens capsular bag before capsulotomy.

In the above, a pharmaceutical composition kit can be provided, using the treating composition, and an inhibiting composition comprising, in an effective amount, an inhibitor for inactivating or blocking the proenzyme upon introduction of the pharmaceutical composition into the anterior chamber.

Another important aspect of the present invention is a method for separating lens epithelial cells and preventing posterior capsular opacification, comprising the steps of: making an incision in the anterior part of the eye; making a hole or an opening in the lens capsule; introducing the aforesaid treating composition into the lens capsular bag, wherein the focal contact-modulating substance or proenzyme modulates focal contacts directly or via a substance generated from the focal contact-modulating substance or proenzyme to mediate an adhesion between the lens epithelial cells and the lens capsule; and, causing said focal contact-modulating substance or proenzyme to separate the lens epithelial cells from the lens capsule.

According to the present invention, by using a focal contact-modulating substance or a proenzyme, focal contacts, which mediate adhesion between lens epithelial cells and the lens capsule, can effectively be attacked to separate the interface between lens epithelial cells and the lens capsule with minimized damage to other cells.

The present invention provides improved methods for preventing posterior capsular opacification to eliminate YAG laser capsulotomy in surgically difficult situations and cases and challenging cases that may result in incomplete removal or separation of lens epithelial cells.

Methods for preventing posterior capsular opacification and eliminating YAG laser capsulotomy comprise inserting an ocular implant and introducing a treating solution into the lens capsular bag, wherein said ocular implant, having a property to reduce the development of posterior capsular opacification, is a posterior chamber IOL or a capsular ring, wherein said treating solution has a property or properties to separate lens epithelial cells and prevent the proliferation of remnant lens epithelial cells after cataract surgery. The treating solution comprises a focal contact-modulating substance or a proenzyme.

Another important aspect of the present invention is to provide methods for eliminating YAG laser capsulotomy without causing any significant damage to the lens capsule and the zonules, in surgically difficult situations and cases and challenging cases, comprising inserting an ocular implant and introducing a proenzyme into the lens capsular bag, wherein said ocular implant, having a property to reduce the development of posterior capsular opacification, is a posterior chamber IOL or a capsular ring. AL biconvex IOL with truncated sharp posterior optic edge, a convex-plano (plano-posterior) IOL or a concave-posterior IOL is used for the posterior chamber IOL. It was found that YAG laser capsulotomy is eliminated by the use of an agent alone or the synergistic effect with implantation of an ocular implant that has a property to reduce the development of posterior capsular opacification. The possibility to eliminate YAG laser capsulotomy is maximized and elimination of the YAG laser capsulotomy is achieved in surgically difficult situations and cases and challenging cases.

DETAILED DESCRIPTION OF THE PREFERRED EMBODIMENTS

In order to develop a method to separate lens epithelial cells, it is necessary to know what kinds of structures are formed between lens epithelial cells and the lens capsule. This aspect has not been evaluated in detail in the literature. In the present invention, the localization of structures that mediate the adhesion between lens epithelial cells and the lens capsule is elucidated. The inventor has found that structures called "focal contacts" are densely formed in the lens epithelial cells toward the equator of the lens, and that these structures are resistant to cell separation. Based on this discover(, compositions and methods have been developed to modulate focal contacts and release the adhesion mediated by focal contacts, in order to separate lens epithelial cells from the lens capsule.

Also, in the present invention, damage to the zonules can be avoided even when a treating solution has contact. Damage to the zonules is a substantial problem when am active enzyme is used. The damage can be eliminated by the use of a proenzyme that has little or no enzyme activity itself A proenzyme may be rendered to bind to lens epithelial cells. Activation of the cell-bound proenzyme may be induced by activators present on the lens epithelial cell surface and/or by activators which are introduced exogenously. The enzyme generated from the proenzyme on the cell surface releases the adhesion between the lens epithelial cells and the lens capsule, and induces the separation of the interface between the lens epithelial cells and the lens capsule (herein after referred to as "lens epithelial cell separation" or "separation of lens epithelial cells"). Lens epithelial cell separation can be achieved by a proenzyme solution with no addition of its activators.

Further, in the present invention, the effect of a treating solution is limited to lens epithelial cells, thereby lowering the risk of surgery prior to, during, and after capsulotomy. This can be achieved by an introduction of a mixture of an inhibitor and a viscoelastic material into the anterior chamber.

In addition, in the present invention, the efficacy of a treating solution can be increased by introduction of an inhibitor into the lens capsular bag.

Other objects, features, and advantages of the present invention will become apparent from the detailed description of the invention that follows.

Structures between lens epithelial cells and the lens capsule

In order to develop a procedure to separate the interface between lens epithelium cells and the lens capsule, adhesion between lens epithelial cells and the lens capsule should be released. To develop a method to release the adhesion between lens epithelial cells and the lens capsule, it is necessary to know what kinds of structures are formed between lens epithelial cells and the lens capsule.

To date several structures are known to be formed in many types of cells between cells and their underlying substratum (substrate) in vitro or between cells and the extracellular matrix in vivo. These structures mediate adhesion between cells and the underlying substratum or between cells and the extracellular matrix. The specialized sheet-like extracellular matrix that is found in close proximity to endothelial, epithelial, fat, muscle, and nerve cells is called "basement membrane" (Mosher et al., *Curr Opin. Cell Biol.*, 4:810–18, 1992). Hemidesmosomes, integrins, and focal contacts are the characteristic structures that are formed between cells and the underlying substratum or between cells and the extracellular matrix. Among these structures, hemidesmosomes can be seen by transmission electron microscopy (TEM). In contrast, integrins and focal contacts cannot be identified by TEM unless an immunohistochemical technique is employed. Our current knowledge of structures between lens epithelial cells and the lens capsule (basement membrane of the lens epithelial cells) is largely dependent on the observation using TEM, and until recently immunohistochemical techniques have not frequently been used. In the lens, no typical hemidesmosomes are formed between lens epithelial cells and the lens capsule. Recently the localization of several integrins in the lens has been elucidated by using immunofluorescence microscopy (Menko et al., *Exp. Cell Res.*, 218:516–21, 1995). However, no study in the literature has shown the localization of focal contacts in the lens.

Although hemidesmosomes and intergrins contribute to cell adhesion, focal contacts are the most important target. Hemidesmosomes are formed in certain epithelial cells and are not typically formed in the lens with the only one exception, hemidesmosome-type condensation. Integrins are known to be susceptible to depletion of divalent cations. Dissociation of integrin structures can be induced by depletion of divalent cations. Thus, when a treating solution includes a metal chelating agent such as EDTA, adhesion mediated by integrins can be released or weakened to separate lens epithelial cells. In contrast, focal contacts are resistant to the depletion of divalent cations. Accordingly, mainly the modulation of focal contacts must be considered in order to separate the lens epithelial cells.

Elucidation of the localization of focal contacts in the lens

When cultured cells form contacts with their underlying substratum, cultured cells adhere tightly to the underlying substratum Through discrete regions of the plasma membrane. These regions are referred to as focal contacts, focal adhesions or adhesion plaques (Burridge et al., *Annu. Rev. Cell Biol.*, 4:487–525, 1988). Components of focal contacts include actin, α-actinin, ezrin, focal adhesion linase, fimbrin, integrin, moesin, paxillin, radixin, talin, tensin, tenuin, vinculin, urokinase plasminogen activator (uPA) add urokinase receptor (urokinase type plasminogen activator receptor) (Geiger et al., *Cell Motil. Cytoskeleton,* 20:1–6, 1991; Pollanen et al., *Adv. Cancer Res.*, 57:273–82, 1991). Among these, talin and vinculin are proteins whose characteristics are well known and which are specifically localized at focal contacts in contact sites between cells and the underlying substratum (Burridge et al., 1988; Geiger et al., 1991).

Although no study has shown the presence of focal contacts in the lens, the present inventor has elucidated localization of focal contacts in human and porcine lenses by using immunofluorescence microscopy. Presence of focal contacts was determined by the fluorescence for the specific proteins, talin and vinculin at contact sites between lens epithelial cells and the lens capsule. The present inventor has found that focal contacts are extensively formed in the lens epithelial cells toward the equator of the lens and almost absent (or not extensive in any case) in the lens epithelial cells in the anterior portion of the lens. The term anterior portion means, herein, the anterior one-third of the area between the anterior pole and the lens equator.

Resistance of focal contacts to cell separation has been evaluated using cultured human lens epithelial cells. It is confirmed that focal contacts are resistant to extracellular-calcium depletion that is caused by an EDTA solution. In this connection, it was reported that when EDTA was included in an irrigative solution and a simulated extracapsular cataract extraction was performed in cadaver eyes, lens epithelial cells in the anterior portion of the lens could be separated from the lens capsule (Humphry et al., 1988), but not the differentiating lens epithelial cells toward the lens equator. Accordingly, it became clear that focal contacts are extensively formed toward the lens equator and the differentiating lens epithelial cells which extensively form focal contacts cannot be separated by an EDTA solution alone.

Based on this discovery of the concentrated localization of focal contacts in the differentiating lens epithelial cells toward the lens equator, compositions and methods have been developed to release the adhesion mediated by focal contacts and separate lens epithelial cells from the lens capsule.

Lens epithelial cell separation by modulation of focal contacts

In accordance with the present invention, any solution that modulates focal contacts and releases the adhesion that is mediated by focal contacts between lens epithelial cells and the lens capsule can be employed as a solution of a focal contact modulating substance to separate lens epithelial cells from the lens capsule. The tern "focal contact-modulating substance" means, herein, an agent itself having a property or properties to modulate focal contacts or an agent that generates a substance that has a property or properties to modulate focal contacts. A focal contact modulating substance is included in a treating solution and the lens epithelial cells are separated by a treating solution. The term "a treating solution" means, herein, a solution having a property or properties to separate lens epithelial cells and prevent the proliferation of remnant lens epithelial cells after cataract surgery. Thus, in accordance with the present invention, any solution having a property or properties to separate lens epithelial cells may be used as a treating solution. A treating solution can include one or more types of focal contact-modulating substance, and one or more treating solutions can be used to generate a substance to separate lens epithelial cells.

One group of substances that may be used for a focal contact modulating substance is oxidants such as monochloramines and hypochlorous acid, which can be used to disrupt focal contacts. Another group of substances that may be used are those having a property or properties to modulate urokinase receptors and/or plasminogen activators that bound to urolinase receptors on the cell surface. The substances to be used include, but not limited to, phosphatidylinositol-specific phospholipase C, kaliikrein, plasminogen, plasmin, complex of either streptokinase or staphylokinase with either plasminogen, plasmin, or both, anisoylated plasminogen streptokinse activator complex (APSAC), and urokinase type plasminogen activators. By using a simple screening procedure employing cultured human lens epithelial cells, relative efficacy of focal contact modulating substances to be used may be determined. Preferably plasminogen is used for a focal contact modulating substance. The reasons are described in the following section. In the above, an appropriate concentration of a focal contact-modulating substance depends on the type of focal contact-modulating substance. In general, the concentration of a focal contact modulating substance is in the range of from 0.001% to 10%, preferably from 0.01% to 2.0%.

Use of proenzyme

One of the embodiments of the present invention is to provide compositions and methods that do not cause any damage to the zonules even when a treating solution has contact. It can be achieved by the use of a proenzyme.

A proenzyme has little or no enzyme activity and in itself does not damage any tissue. In accordance with the present invention, any proenzyme may be used in a treating solution to induce the separation of lens epithelial cells on activation. By definition, proenzymes and focal contact modulating-substances overlap with each other but are not identical as described later.

In order to separate lens epithelial cells from the lens capsule, a solution of a proenzyme may be introduced into the lens capsular bag. The introduced proenzyme may be rendered to bind to its receptors on lens epithelial cells for a sufficient time. The cell-bound proenzyme may be activated by its activators present on the cell surface and/or by further introducing a solution of its activators exogenously. The enzyme generated from, the proenzyme on the cell surface releases the adhesion between lens epithelial cells and the lens capsule, and induces the separation of the lens epithelial cells.

A solution of a proenzyme to be introduced is prepared in a physiologically acceptable solution, which includes, but is not limited to, saline, phosphate-buffered saline, or the like.

A proenzyme from any source can be used in accordance with the present invention. A proenzyme to be used may be of human, animal, recombinant, or synthetic origin. Proenzymes to be used may be in proteolytically induced forms induced from ;a proenzyme of the native form as long as the induced forms retain the character of proenzymes, i.e., having little or no enzyme activity and exhibiting apparent enzyme activity upon activation. Recombinant proenzymes to be used may be variants of a proenzyme as long as the recombinant proenzymes retain the above character. Alternatively, proenzymes may be hybrid proteins as long as the proteins retain the above character. Because of the species specificity of proenzyme activation, a proenzyme from a human source or a recombinant human proenzyme is suitable. The proenzyme to be used is preferably a proenzyme of a serine (serene) protease (proteinase). Proenzymes of serine proteases to be used include, but are not limited to, plasminogen, prokallikrein and coagulation factor XII. In a model using cultured human lens epithelial cells, relative efficacy of proenzymes to be used may be determined. Plasminogen is more preferably suited to be used. This is because uPA is localized at focal contacts (Pöllanen et al., *J. Cell Biol.*, 106:87–95, 1988) and, by introducing a sufficient amount of plasminogen, extensive generation of plasmin can be induced at focal contacts, which efficiently releases the adhesion mediated by focal contacts to separate lens epithelial cells. Plasminogen to be used includes, but is not limited to, native plasminogen (Glu-plasminogen), Lys-plasminogen, Val$^{354}$-plasminogen (Powell et al., *Biochem Biophys Res Comm.*, 102:46–52, 1981), mini(-)plasminogen (Sottrup-Jensen et al., *Prog Chem Fibrinol Thrombol,* 3:191–209, 1978), micro(-)plasminogen (U.S. Pat. No. 4,774,087 to Wu et al 1988) and combinations of two or more members of this group. Glu-plasminogen has glutamic acid in the amino-terminal position (Wallén et al., *Biochim. Biophys. Acta,* 221:20–30, 1970). Lys-plasminogen is a collective name to denote proteolytically modified forms of Glu-plasminogen in which a polypeptide is cleaved from the NH$_2$-terminus. Lysine, methyonine and valine have been detected as N-terminal amino acids of Lys-plasminogen (Wallén et al., 1970). Val$^{354}$-plasminogen, mini(-)plasminogen and micro(-)plasminogen are also the forms that enzymatically derived from Glu-plasminogen. As mini (-)plasminogen, Val$^{442}$-Asn$^{791}$ or neo-plasminogen-Val$^{442}$ (Sottrup-Jensen et al. 1978), Ala$^{444}$-Asn$^{791}$ (Lasters et al., *Eur. J. Biochem.,* 244:946–52, 1997), Val$^{442}$-Asn$^{790}$ (Wu et al., *Biochem Biophys Res Comm.,* 188:703–11, 1992), and Val$^{443}$-Asn$^{791}$ (Misselwitz et al., *Int. J. Biol. Macromol.,* 16:187–94, 1994) are known and usable. As micro(-) plasminogen, Lys$^{530}$-plasminogen and Leu$^{531}$-plasminogen (U.S. Pat. No. 4,774,087 to Wu et al 1988), Ala$^{543}$-Asn$^{719}$ (Lasters et al., 1997), and Lys$^{531}$-Asn$^{791}$ (Misselwitz et al., 1994) are known and usable. Val$^{354}$-plasminogen, mini(-) plasminogen, and micro(-)plasminogen contain the catalytic triad of plasmin (His$^{603}$, Asp$^{646}$, and Ser$^{741}$) and can be activated into plasmin. Lys-plasminogen can particularly be suitably used. This is because, by using Lys-plasminogen, plasmin generation can be induced rapidly (Pannell et al., *Blood,* 67:1215–23, 1986) to separate lens epithelial cells. In addition, due to the relatively large molecular weight (80, 000), the introduced Lys-plasminogen can be confined in the lens capsular bag until capsulotomy is completed. Alternatively, Glu-plasminogen can be used with lysine to induce a rapid generation of plasmin.

With regard to sources of plasminogen, a recombinant protein is suitably used in order to avoid viral transmission (U.S. Pat. No. 5,304,383 to Eible et al., 1994). Due to the presence of activators, the preparation of intact human plasminogen from a mammalian cell system is not successful. However, using insect cells, human plasminogen can be obtained (Whitefleet-Smith et al., *Arch Biochem Biophys.,* 271:390–99, 1989).

When plasminogen binds to a cell, the binding is mediated by its specific receptors on the cell. Although the molecular nature of the plasminogen/plasmin-binding sites has remained elusive (Pöllänen et al., 1991), the binding of plasminogen to a cell is almost ubiquitous. Therefore, a sufficient amount of plasminogen can be bound to lens epithelial cells to generate plasmin and separate the lens epithelial cells. Actually, in an in vitro model, lens epithelial cells could efficiently be separated by a Lys-plasminogen solution.

In order to generate plasmin, plasminogen must be activated by activators. Physiologically, urokinase plasminogen activators mediate the activation of plasminogen into plasmin. Urokinase plasminogen activators are present in the form of single-chain urokinase plasminogen activator (scuPA) or double-chain urokinase plasminogen activator (tcuPA). Natural scuPA is a proenzyme that has little or no proteolytic activity against the natural substrate plasminogen and activated by limited proteolysis into an active enzyme, tcuPA. tcuPA activates its physiological substrate Glu-plasminogen into Glu-plasmin by, cleavage of the Arg$^{560}$-Val$^{561}$ peptide bond (Robbins et al., *J. Biol. Chem.,* 242:233–342, 1967). Glu-plasmin is readily converted to Lys-plasmin by autocatalysis (Danø et al., *Adv Cancer Res.,* 44:144–6, 1985). tcuPA also catalyzes conversion of Lys-plasminogen to double-chain active Lys-plasmin by cleavage of the Arg$_{560}$-Val$_{561}$ bond. Thus, tcuPA can activate both Glu-plasminogen and Lys-plasminogen into plasmin. tcuPA can also activate Val$^{343}$-plasminogen, mini(-)plasminogen and micro(-)plasminogen into Val$^{354}$-plasmin, mini(-) plasmin and micro(-)plasmin, respectively. In turn, the generated plasmin induces conversion of scuPA into tcuPA. In this manner, plasmin can be generated exponentially where uPA and plasminogen are present.

One of the advantages in using plasminogen is that the enzyme activity can be induced extensively at focal contacts.

This is because uPA binding to a cell is mediated by urokinase receptors (UPAR) and uPA are localized at focal contacts and cell-to-cell contacts (Pollanen et al., 1988). Therefore, by introducing a higher concentration of plasminogen, plasminogen can be activated at focal contacts and cell-to-cell contacts where uPA is located. That is, plasmin can be generated exponentially at focal contacts and cell-to-cell contacts. Plasmin generation at focal contacts can cause disruption of focal contacts and effectively releases the adhesion mediated by focal contacts to lead to the separation of the lens epithelial cells.

In a cultured human lens epithelial cell model, when lens epithelial cells are exposed to Glu-plasminogen or Lys-plasminogen solutions of various concentrations and for various time periods, cell lysis can be induced by a plasminogen solution alone. Indeed, without adding activators, lens epithelial cells can efficiently be separated by a plasminogen solution. The plasminogen activators are expected to be present on the lens epithelial cell surface.

In the lenses with some types of cataracts such as posterior subcapsular cataracts, lens epithelial cells may migrate into a site or sites on the lens capsule where the lens epithelial cells are physiologically not present. It is also found in an in vitro model (e.g., Examples 1 and 2) that single cells can be separated by plasminogen solution alone. Thus, migrating lens epithelial cells can also efficiently be separated by a plasminogen solution.

A structure called "tight junction" is formed between lens epithelial cells except in the lens equator (Lo et al., *Invest. Ophthalmol. Vis. Sci.*, 24:396–402, 1983, Lo, *Exp. Eye. Res.*, 45:393–406, 1987). This structure limits the passage of substances between lens, epithelial cells. In order to separate lens epithelial cells at focal contacts, the passage of a treating solution into the space between the lens epithelial cells and the lens capsule should be secured. For this purpose, a calcium chelating agent or a salt thereof may be included in a treating solution when the size of capsulotomy is not sufficiently large. This is.; because in the lens epithelial cells toward the anterior portion of the lens, the tight junction is formed between the cells. A calcium chelating agent induces depletion of extracellular calcium ions. That causes break-down of the barrier function of the tight junction between the lens epithelial cells so that the passage of the treating solution to the space between the lens epithelial cells and the lens capsule is secured. In this operation, the diameter of capsulotomy may be approximately 7.0 mm or smaller. Technologically, performance of capsulotomy is easier when the diameter is small.

When applying to the methods of prevailing cataract surgery, a chelating agent such as EDTA may be included in a treating solution. This is because in the procedures, the size of the capsulotomy is not large, e.g., equal to or less than 6.5 mm, usually larger than 5.0 mm. However, when capsulotomy of a large size is performed, a treating solution may not include a chelating agent in order to separate lens epithelial cells. This is because only the lens epithelial cells in the lens equator remain after capsulotomy (lens epithelial cells formed toward the anterior portion are removed from the eye with attached lens capsule). These cells can be separated by a treating solution without a chelating agent, because no tight junction is present in the lens equator. In addition, due to the extensive formation of focal contacts in the lens equator, extensive generation of plasmin, for example, can be induced to separate lens epithelial cells. In some cases with pathologies, it is quite difficult to fully dilate pupil by using mydriatics and complete a large capsulotomy (e.g., in the case of glaucoma or diabetes). In any event that capsulotomy of a large size can be performed, a chelating agent can be omitted from a treating solution, and can be included in a separate solution as necessary.

To separate lens epithelial cells by a plasminogen solution, a relatively large capsulotomy may preferably be performed in the prevailing extracapsular cataract extraction. This is because focal contacts are not extensively formed in the lens epithelial cells toward the anterior portion of the lens. Although these cells are taken away with the lens capsule (anterior capsule) when capsulotomy is completed, mainly, differentiating; lens epithelial cells, on which surface uPA is extensively expressed, still remain in the capsular bag after capsulotomy. As described above, these lens epithelial cells can effectively be separated by a plasminogen solution alone. In this operation, the diameter of the capsulotomy may be equal to or larger than 5.0 millimeters, approximately.

When the present invention is conducted in cataract surgery, after a small hole is; made in the lens capsule, a treating solution may be introduced into the lens capsular bag via a fine needle or cannula with a positive pressure. Alternatively, the treating solution .may be introduced into the lens capsular bag through two or more holes. A treating solution separates the interface between the lens epithelial cells and the lens fibers. This is because the adhesion between the lens epithelial cells and the lens fibers is not so strong as the adhesion between the lens epithelial cells and the lens capsule. When a proenzyme is used for an agent in a treating solution, a proenzyme may be rendered to flow between the lens epithelial cells and bind to the lens epithelial cells for a sufficient time. The entire procedure of the prevailing method of extracapsular cataract surgery can be completed in thirty minutes in most cases. In the above, the practically acceptable time for surgery is approximately less than five minutes which is required to cause a sufficient proenzyme lo bind to the cells in order to separate the lens epithelial cells. For example, using a Lys-plasminogen solution at concentrations of 18 micromol/l (hereafter referred to as $\mu$m) or higher, cultured human lens epithelial cells can almost completely be separated in four minutes (e.g., Example 2). When Lys-plasminogen is used for a proenzyme, due to the relatively large molecular weight (80,000), the introduced Lys-plasminogen can be confined in the lens capsular bag until capsulotomy is completed.

The total volume of a solution or solutions to be introduced into the lens capsular bag may be between 4 microliters (hereafter referred to as $\mu$l) and 250 $\mu$l. Preferably, tie total volume to be introduced into the lens capsular bag may not exceed 20 pi, and more preferably, the total volume may be approximately between 12 $\mu$l and 18 $\mu$l for an adult lens. For pediatric cataracts, the volume of a treating solution to be introduced may be reduced depending on the lens volume. For optimal generation of an enzyme, a treating solution may be warmed to 37° C. prior to use. Consistently with the above, U.S. Pat. No. 4,078,564 to Spina et al., 1978 teaches that 20 microliters of a solution can be introduced without increasing the intralenticular pressure to a level in which rupture of the lens capsule occurs.

In the above, an appropriate concentration of a proenzyme depends on the type of proenzyme. In general, the concentration of a proenzyme is in the range of from 0.001%) to 10%, preferably from 0.01% to 2.0%. If the proenzyme has a relatively low molecular weight (e.g., Val$^{354}$-plasminogen: 48,000, mini(-)plasminogen: 38,000) such that the proenzyme is likely to pass through the lens capsule and to escape from the lens capsular bag (preferably molecular weight is approximately 70,000 or higher) (Friedenwald, *Arch*

Ophthalmol., 3:182–93, 1930), or if the proenzyme lacks a binding site for binding to cells (e.g, micro(-)plasminogen lacks part of kringle 5), a relatively higher concentration of the proenzyme needs to be used (increased by approximately 10-fold). In the above case, to protect areas other than the target area, the use of an inhibitor (described later) is effective.

Other than the foregoing, any proenzyme, which itself does not damage cell.,, which generates a substance facilitating separation of the lens epithelial cells, which binds to the lens epithelial cells, which does not pass through the lens capsule, and preferably which is activated by an activator naturally present in the focal contacts, may be used.

The lens epithelial cells that are separated from the lens capsule by a proenzyme solution are washed away from the eye with irrigating solution, when the residual lens cortex is removed.

In the foregoing, by definition, plasminogen and urokinase type plasminogen activators, for example, function as a focal contact modulating-substance as well as a proenzyme. Phosphatidylinositol-specific phospholipase C, monochloramine, kaliikrein, plasmin, complex of either streptokinase or staphylokinase with either plasminogen, plasmin, or both, and anisoylated plasminogen streptokinase activator complex (APSAC), for example, function as a focal contact modulating-substance but not as a proenzyme. In the above, the complexes are collectively categorized in a focal contact-modulating substance due to the enzyme activity of the complexes. Trypsinogen, for example, functions as a proenzyme but not as a focal contact modulating-substance. The focal contact-modulating substances can be used in a way similar to the proenzymes described above, with respect to, e.g., their concentrations and a carrier.

Use of an inhibitor

One embodiment of the present invention is to provide compositions and methods for limiting the effect of a treating solution to lens epithelial cells prior to, during, and after capsulotomy. It can be achieved by introduction of an inhibitor into the anterior chamber. The term "an inhibitor" means, herein, a substance having a property or properties to limit to lens epithelial cells the effect of a treating solution, wherein the effect is caused by an agent in a treating solution or a generated substance that is generated from an agent. It should be appreciated that an inhibitor per se has no effect on cells or tissues. Furthermore, what is critically important for surgery is that surgical manipulation does not raise the risk of the surgery. For this purpose, an inhibitor may be introduced into the-, anterior chamber as a mixture with a viscoelastic material. The term "mixture", herein, means a physical mixture of an inhibitor and a viscoelastic material or a formed complex between an inhibitor and a viscoelastic material by mixing.

When a solution of an inhibitor does not include a viscoelastic material and is introduced into the anterior chamber, a solution of an inhibitor leaks from the eye through the incision in the anterior part of the eye and the anterior chamber depth decreases or almost disappears during surgery in the following steps: When a treating solution is introduced into the lens capsular bag, when capsulotomy is performed and/or when the lens nucleus is delivered from the eye. There is a great risk for the corneal endothelium 110 be damaged by a surgical manipulation or surgical manipulations. Indeed, an agent or a generated substance in a treating solution that is introduced into the lens capsular bag can escape from the lens capsular bag, have contact with the cells and the tissues facing the anterior chamber, and damage them. Therefore, the simple introduction of an inhibitor into the anterior chamber is not a reliable method to ensure the safety of the surgery. In contrast, when an inhibitor is introduced into the anterior chamber with a viscoelastic material, the anterior chamber depth is maintained prior to, during, and after capsulotomy, and the effect of a treating solution can be limited to lens epithelial cells. Accordingly, what was found is that, by introducing a mixture of an inhibitor and a viscoelastic material into the anterior chamber, the effect of a treating solution can be limited to lens epithelial cells and the surgery can be performed without raising risks during surgery.

A solution of an inhibitor to be introduced is prepared in a physiologically acceptable solution, which includes, but is not limited to, saline, phosphate-buffered saline or the like.

In accordance with the present invention, an inhibitor form any source may be used. Inhibitors to be used may be of natural, recombinant, or synthetic origin. The timing of introduction of an inhibitor-containing solution will be described later. Inhibitors to be used may be substances having a property or properties of binding to an agent in a treating solution and inhibiting the binding of an agent to cells. The inhibitors include, but are not limited to, an antibody against plasminogen (Church et al., *Hybridoma.,* 10:659–72, 1991) and a lysine-binding-site (LBS)-binding substance that has a property or properties of binding to at least one of the lysine-binding sites of plasminogen. The lysine-binding-site-binding substances include, but are not limited to, $\alpha_2$-antiplasmin, histidine-rich glycoprotein, $\omega$-amino acids, poly-lysine and a poly-lysine derivative. $\omega$-amino acids include 6-aminohexanoic acid, trans-4-(aminomethyl)-cyclohexanecarboxylic acid (tranexamic acid), lysine and p-aminomethyl benzoic acid. Alternatively, inhibitors to be used may be substances having a property or properties of binding to receptors on cells and inhibiting the binding of an agent to the cells. These inhibitors include, but are not limited to, lipoprotein(a), apoprotein(a), an antibody against plasmin(ogen) receptors and a variant of plasminogen that cannot be activated into plasmin. Alternatively, inhibitors to be used may be substances having a property or properties of inhibiting an activator of an agent. These inhibitors include, but are not limited to, serine protease inhibitors. The serine protease inhibitors to be used may be plasminogen activator inhibitors such as PAI-1, PAI-2, PAI-3 and protease nexin. Alternatively, inhibitors to be used may be substances having a property or properties of inhibiting a generated substance that is induced from an agent in a treating solution. These inhibitors include, but are not limited to, serine protease inhibitors and an antibody against plasmin. The serine protease inhibitors may be plasmin inhibitors including $\alpha_2$-antiplasmin, aprotinin, diisopropyl fluorophosphalte, 1-chloro-3-tosylamido-7-amino-L-2-heptanone (TLCK), $\alpha_1$-proteinase inhibitor, $\alpha_2$-macroglobulin, surarin, antithrombin III and C1-esterase inhibitor. Alternatively, inhibitors to be used may be an antagonist of an agent in a treating solution, wherein the antagonist is not described above. The inhibitors include, but are not limited to, L-methionine.

All these inhibitors described above can be used to limit the effect of a treating solution to lens epithelial cells. By using an in vitro or in vivo model (e.g., Experiment 2), relative efficacy of inhibitors to be used can be determined.

Among the inhibitors, a trapping substance is suitable to efficiently limit the effects of a treating solution to lens epithelial cells during and after capsulotomy. The trappings substance may be introduced into the anterior chamber and/or into the lens capsular bag as a mixture with a viscoelastic material. The term "trapping substance", herein, means an inhibitor having a property or properties of binding to an agent or binding to or inhibiting a generated substance in a treating solution.

In a viscoelastic material, diffusion of a substance is slow so that a trapping substance in a viscoelastic material can effectively bind to an agent or bind to or inhibit a generated substance in a treating solution before an agent or a generated substance which is escaping from the lens capsular bag reaches the cells and the tissues facing the anterior chamber. This feature is distinct for trapping substances because a trapping substance directly acts on an agent or a generated substance.

To efficiently limit the effect of a treating solution to lens epithelial cells during capsulotomy and reduce the concentration of a trapping substance to be introduced into the anterior chamber, a trapping substance may be introduced into the lens capsular bag prior to capsulotomy (any time before capsulotomy, e.g., immediately before or 1–10 minute before capsulotomy). A solution of a trapping substance which is introduced into the lens capsular bag coats the inner side of lens capsule of capsulotomy. Until capsulotomy is performed, an agent or a generated substance in a treating solution can be confined in the lens capsular bag. Therefore, a trapping substance can efficiently bind to an agent or bind to or inhibit a generated substance in the lens capsular bag and reduce the concentration of the trapping substance to be introduced into the anterior chamber. In this connection, simply by introducing an inhibitor into the lens capsular bag, the introduction of an inhibitor into the anterior chamber can be omitted. A trapping substance may be introduced into the lens capsular bag as a mixture of the trapping substance and a viscoelastic material.

The effect of a treating solution can be more efficiently limited to lens epithelial cells when a trapping substance is or trapping substances are introduced into both the anterior chamber and the lens capsular bag. In this operation, a trapping substance which is introduced into the anterior chamber may be the same as that introduced into the lens capsule, or they may be different. A trapping substance is preferably introduced into the anterior chamber as a mixture with a viscoelastic material to maintain the anterior chamber depth. On the other hand, a solution of a trapping substance to be introduced into the lens capsular bag preferably does not include a viscoelastic material. This is because a trapping substance in the capsular bag can quickly limit the effect of a treating solution within a short time which is acceptable for surgery, and thus reduce the concentration of a trapping substance to be introduced into the anterior chamber. When a solution of a trapping substance is introduced into the lens capsular bag, the solution coats the inner side of the lens capsule so that the trapping substance can efficiently bind to an agent or bind to or inhibit a generated substance. As a result, if a solution of a trapping substance is introduced into the anterior chamber, the concentration of the trapping substance can be reduced.

Introduction of a trapping substance-containing solution into the lens capsular bag can be performed singly or in combination with introduction of a trapping substances containing solution into the anterior chamber. In addition, a solution of a substance having a property or properties of inhibiting a generated substance, other than trapping substance-containing solutions, can be used in cooperation with the trapping substance-containing solution.

Introduction of a trapping substance-containing solution into the lens capsular bag is normally performed after, preferably 2–10 minutes after, introduction of a solution containing an active component (focal contact-modulating substance or proenzyme) into the lens capsular bag.

Trapping substances to be used are preferably substances having a property or properties of binding to an agent in a treating solution and inhibiting the binding of an agent to cells. Trapping substances to be used are, more preferably, lysine-binding-site-binding substances. Particularly, ω-amino acids are suited for the lysine-binding-site-binding substances. Among the ω-amino acids, tranexamic acid, 6-aminohexanoic acid and p-aminomethyl benzoic acid can be suitable due to the relatively strong effect of inhibiting binding.

Alternatively, as an inhibitor to be introduced into the lens capsular bag, a substance having a property or properties of inhibiting a generated substance may be used. Preferably an aprotinin of either natural or recombinant origin or a recombinant aprotinin variant can be used for this purpose. An inhibitor or a trapping substance to be used for the lens capsular bag is preferably contained in a solution in an amount between 10 $\mu$M and 20,000 $\mu$M (0.01 mM and 20 mM) approximately, more preferably between 20 $\mu$M and 10,000 $\mu$M (0.02 mM and 10 mM). The volume of the inhibitor to be introduced into the lens capsular bag may be approximately 3 to 15 $\mu$l, preferably 5 to 10 $\mu$l. The volume of the inhibitor to be introduced into the anterior chamber may be approximately 5 $\mu$l to 250 $\mu$l, preferably 150 $\mu$l to 200 $\mu$l. An inhibitor or a trapping substance to be used for the anterior chamber, preferably with a viscoelastic material, is introduced at a concentration between 2 $\mu$M and 20,000 $\mu$M (0.002 mM and 20 mM) approximately, more preferably between 5 $\mu$M and 10,000 $\mu$M (0.005 mM and 10 mM).

In accordance with the present invention, a viscoelastic material from any source can be used. Viscoelastic materials to be used may be of natural or synthetic origin. Preferred viscoelastic materials to be used include, but are not limited to, hyaluronic acid, a salt thereof, hydroxypropylmethylcellulose, methylcellulose, carboxymethyl cellulose, 20 ethyl cellulose, collagen, chondroitin sulfate, a salt thereof, polyacrylamide, CELLUGEL® (synthetic polymer of modified carbohydrate having a molecular weight of 100,000; Vision biology Inc., California), proteoglycans, keratin of various molecular weights, and combinations of two or more members of this group. More preferably, sodium hyaluronate, hydroxypropylmethylcellulose and a mixture of sodium chondroitin sulfate and sodium hyaluronate are suitable to be used. The viscoelastic material can be used in an amount of 0.01 to 10%, preferably 1.0 to 4.0% in a solution containing an inhibitor or trapping substance.

Use of a calcium chelating agent

As described above, a structure called "tight junction" is formed between lens epithelial cells except in the lens equator (Lo et al. 1983, Lo 1987). This structure limits the passage of substances between lens epithelial cells. In order to separate lens epithelial cells at focal contacts, the passage of a treating solution into the space between the lens epithelial cells and the lens capsule should be secured. For this purpose, a calcium chelating agent or a salt thereof may be included in a treating solution. A calcium chelating agent induces the depletion of extracellular calcium ions. It causes the break-down of the barrier function of the tight junction between the lens epithelial cells so that the passage of a treating solution is secured.

The calcium chelating agent to be used may be EDTA or ethylene glycol bis(2-aminoethyl ether)-N,N,N',N'- tetraacetic acid (EGTA). Due to the stronger effect, EDTA is particularly suitable for the calcium chelating agent.

Additionally, integrin moleculars can be dissociated by the depletion of divalent cations (Tozer et al., *Biochem Cell Biol.*, 74:785–98, 1996) so that the adhesion mediated by integrins can be released or weakened by the use of a metal chelating agent, preferably by EDTA. EDTA can cooperatively work with a focal contact-modulating substance or a proenzyme to separate lens epithelial cells located toward the anterior portion of the lens.

The safety of the use of EDTA solution in the eye has been evaluated clearly in detail in the literature (U.S. Pat. No. 5,204,331 to Nishi et al., 1993; Nishi et al., 1993).

The calcium chelating agent can be used in an amount of 0.5 mM to 100 mM in a treating solution. In particular, preferably, when EDTA is used, its concentration is in the range of 15 mM to 50 mM, and when EGTA is used, its concentration is in the range of 2 mM to 5 mM.

Use of a dye

Additionally, a dye may be included in a treating solution or a solution of am inhibitor so that the introduction of a specific solution into the intended site or sites in the eye can be assured. Preferably a dye is included in a solution of an inhibitor which is introduced into the lens capsular bag. Usable dyes include fluorescein, an alkalimetal salt thereof, and methylene blue. The dye can be used in an amount of 0.0001 to 1% in a treating solution.

Establishment of Lens Epithelial Cell Culture Model to Evaluate Agents

Using an in vitro or in vivo model, relative efficacy of focal contact-modulating substances, proenzymes, and/or inhibitors to be used can be evaluated with high accuracy. For example, the culture model using cultured human lens epithelial cells, shown in Experiment 2 described later, is commonly used in studies. In this model, formation of a cell sheet is very consistent and almost independent of the surgical damage and the source, so that accurate evaluation is possible. Cell culture models are suited for evaluation of agents to prevent posterior capsular opacification. There are many common features; between the in vivo condition in which an agent is used and the in vitro condition in which cells are cultured. There is anatomically no fibrovascular tissue around the lens, and lens epithelial cells form a monolayer on the lens capsule like a cell culture. Protein concentration of the aqueous humor is approximately 0.1%–1% of the serum. When surgery is performed, the protein concentration rises to about 10% of the serum. During cataract surgery, the anterior chamber is irrigated with irrigating solution (balanced salt solution). The condition of the lens in vivo is relatively simple and, using a cell culture model, it is possible to mimic the in vivo condition during cataract surgery, even though the detailed condition must be carefully evaluated and adjusted. In the models of human lens epithelial cell cultures, many basic features are shared. One good example of culturing human lens epithelial cells is the model used by Tarsio et al. (*J. Cataract Refract Surg.*, 23:260–6, 1997; U.S. Pat. No. 5,616,122 to Lam et al 1997). Tarsio et al. cultured human lens epithelial cells with the lens capsule and determined the effective concentration of an immuntoxin to be used for clinical trials. They evaluated the viability of the cells on the lens capsule. A value of inhibition % of the cells, which is determined by trypan blue staining, was used to determine the concentration to be used for the clinical trails. It was projected that four years after cataract surgery, 67% of the patients would require YAG laser treatment due to subsequent development of posterior capsular opacification. In contrast, 18% of the drug-treated patients were projected to need the treatment (Ocular Surgery News, Nov. 1, 1996). It was not clear how they evaluated the heterogenous lens epithelial cells (Due to differentiation, morphological aid biochemical features of lens epithelial cells are not uniform). The clinical result, however, had a relatively good correlation with the results obtained in the culture study. Therefore, generally, it can be said that the results from experiments using cultured human lens epithelial cells well reflect or correspond to the in vivo effect. One of the reasons for such correlation is that an agent is directly introduced into the eye as a part of the surgery, as with in the cultured cell model.

In order to evaluate an agent to separate the lens epithelial cells, the cultured cell model has to have the specific feature that the cell sheet has the structure recognized in the in vivo lens. It is shown in the formed cell sheet (e.g., Experiment 3) that focal contacts are; extensively formed toward the center as noted in the lens epithelial cells from the anterior portion toward the lens equator in vivo. Accordingly, the models are judged to be appropriate to evaluate the effect of agents to modulate focal contacts and separate lens epithelial cells. One point to be noted is that, when the present invention is used for cataract surgery, plasminogen solution, for example, is introduced into the lens capsular bag prior to capsulotomy. Until the introduction of the plasminogen solution, lens epithelial cells and the lens fibers are attached, and the space between the lens fibers and the lens epithelial cells is a "potential" space. By the introduction of the plasminogen solution, it becomes "an anatomically relevant space." Adhesion between the lens epithelial cells and the lens capsule is strong, so that the interface between the lens epithelial cells and the lens fibers, not between the lens epithelial cells and the lens capsule, is always separated. Thus, by the introduction of e.g., the plasminogen solution, the plasminogen solution can act on lens epithelial cells directly at the prepared concentration. One factor to be noted is that, in the model used in the present inventions medium is changed five times, mimicking the irrigation during lens cortex removal and washing out of the viscoelastic materials after implantation of an intraocular lens. Tie volume of the lens (or the lens capsule bag) is approximately 0.2 ml. The lens capsular bag is irrigated with usually 50–100 ml of irrigation solution. Thus, in the in vivo (surgical) condition, the introduced plasminogen solution will be completely washed away. In the in vitro mode (e.g., Experiment 3), plasminogen is washed away by changing fie medium five times (using 2 ml of DPBS for each change), and the result subsequently evaluated. The above difference between the in vivo conditions and the in vitro conditions is not significant with respect to the residual plasminogen in the medium.

In addition to the effect of separating lens epithelial cells, plasminogen solution induced lysis of the cells. It is confirmed in the cultured cell model that the cells remain attached to the culture dishes after exposure to the plasminogen solution, and the lysed cells are dead, which is evaluated by trypan blue staining. This effect will be also present when the present invention is adapted to surgery.

Clinical Application

By estimating the area of the lens epithelial cells to be coated with a treating solution, the minimum volume of the treating solution can be determined. For example, in the human lens of 60 years or older, the distance between the anterior pole and the posterior pole is approximately 5.0 mm. The distance between the equators (equatorial axis) is approximately 9.6 mm. The surface area of the lens is estimated to be 170 mm2. At least a half of the anterior portion of the lens where lens epithelial cells are formed (approximately 85 mm²) should be coated with the treating solution. Before introduction of the treating solution, the interface between the lens epithelial cells and the lens fibers is constructed as a potential space. The lens epithelial cells (approximately 85 mm2) can be coated by approximately 4 µl of the treating solution. The inner side of the entire lens capsular bag can be coated with approximately 8 µl of the treating solution. Accordingly, approximately at least 4 µl of a treating solution may need to be introduced.

In the prevailing method of extracapsular cataract surgery, after capsulotomy, a fluid (generally physiologic saline) is forcibly injected through a fine canulla that is placed immediately underneath the anterior capsule. This procedure is called "hydrodissection" and performed to separate the lens cortex from the lens capsule or separate the lens nucleus from the cortex. In this procedure, the injected fluid disrupts the interface between the lens epithelial cells and the lens fibers in a direction toward the lens equator. Under an operating microscope, surgeons can see the fluid separating the lens fibers from the lens capsule in the equator. Thus, in the practice of the present invention, the introduction of a treating solution and the movement of the treating solution toward the lens equator can be confirmed under an operating microscope.

EXAMPLE

The practice of certain aspects of the present invention is more fully illustrated in the following examples:

Experiment 1: Determination of Localization of Focal Contacts in Porcine and Human Lenses Materials and Method Porcine lenses were obtained from a local slaughter house. A normal human lens was obtained from surgery for subluxation of the lens due to a trauma. The lenses were frozen with isopentane in cold acetone and cut into sections three to six µm thick using cryostat. The frozen sections were fixed with 3.7% paraformaldehyde in Dulbecco's phosphate buffered saline with $Ca^{2+}$ and $Mg^{2+}$ ($DPBS^+$) at room temperature and permeabilized with 0.5% of TRITON X-100 (Sigma, St. Louis, Mo.) in Dulbecco's phosphate buffered saline without $Ca^{2+}$ and $Mg^{2+}$ (DPBS) for 10 minutes at room temperature or with acetone for five minutes at −20° C. After blocking of nonspecific binding with 2% bovine serum albumin (BSA) in $DPBS^-$, the sections were incubated with murine anti-human vinculin (hVIN-1) (Sigma, St. Louis, Mo.) or mouse anti-talin (8d4)(Sigma, St. Louis, Mo.) in $DPBS^-$ with 1% BSA for 30 minutes at room temperature. After washing with $DPBS^-$, the sections were incubated with FITC conjugated goat anti-mouse IgG in $DPBS^-$ with 1% BSA for 30 minutes at room temperature. The specimens were washed with $DPBS^-$ and observed under immunofluorescence microscopy. Omission of the primary antibody or the use of normal serum served as controls.

Result

In porcine lenses, the fluorescence for talin was absent in the anterior portion of the lens and present in the basal side of the lens epithelial cells toward the lens equator as an interrupted linear pattern. The density and the intensity of the fluorescence greatly increased and the fluorescence became linear in the lens equator. In the human lens, the fluorescence for talin was noted in an interrupted linear pattern in the basal side of the lens epithelial cells in the anterior portion of the lens. The intensity of the fluorescence greatly increased toward the lens equator and the fluorescence was almost linear in the lens equator. For vinculin, the fluorescence was present in the basal side of the lens epithelial cells in an interrupted linear pattern in the anterior portion of the human and porcine lenses. The density and the intensity of the fluorescence greatly increased toward the lens equator and the fluorescence was linear or further forming merged spots in the lens equator. A strong fluorescence was also noted in the interface between the lens epithelial cells and the lens fibers and between lens fibers. The intensity of the fluorescence in the interface between the lens epithelial cells and the lens fibers increased toward the lens equator. Controls showed no fluorescence for talin and vinculin at contact sites between the lens epithelial cells and the lens capsule and between the lens epithelial cells and the-, lens fibers. As determined by the presence of the fluorescence for talin and vinculin between the lens epithelial cells and the lens capsule, the findings indicated that focal contacts were present in the basal side of the lens epithelial cells and the density of the florescence increased toward the lens equator.

Experiment 2: Establishment of Lens Epithelial Cell Culture Model for Evaluation of Agents Materials and Method Lens capsules with attached lens epithelial cells were obtained during cataract surgery in sterile condition. The capsules were allowed to attach to the bottom of culture dishes or glass coverslips, and incubated in Eagle's minimum essential medium (E-MEM) supplemented with 10% fetal calf serum at 37° C.

Result

Human lens epithelial cells formed cell sheets around the lens capsules in two weeks. The center of the cell sheet was densely populated with lens epithelial cells of[] square or polygonal morphology. Around the densely populated area of the cell sheet the cells were elongated. In the peripheral area of the cell sheet, cells were present as scattered, well-spread single cells. These morphological differences between the center, midperiphery and periphery were consistent in the established cell sheets. The established cell sheets were used for in vitro evaluation of agents.

Experiment 3: Determination of Localization of Focal Contacts in Cultured Human Lens Epithelial Cell Sheet Materials and Method Localization of focal contacts in a cultured human lens epithelial cell sheet: (Experiment 2) was elucidated by using immunofluorescence microscopy. Localization of focal contacts was determined by the presence of the fluorescence for vinculin as described in Experiment 1.

Result

In the center of the cell sheet where cells were square or polygonal, fluorescent spots were scattered sparsely at cell-substratum contact sites. In some cells the fluorescent spots were almost absent. In the midperipheral area where the cells were elongated, the fluorescent spots were noted in a typical focal contact pattern at cell-substratum contact sites. As compared to the central area of the cell sheet, each fluorescent spot was larger and they were more densely distributed. In the peripheral area of the cell sheet where mainly single cells were located, fluorescent spots were scattered sparsely. In addition to the fluorescent spots in the cell-substratum contact sites, cell-to-cell contacts gave a linear fluorescence in the central and midperipheral areas. It was concluded that focal contacts were densely formed in the midperipheral area of the cell sheet where the cells were elongated. In contrast, in the central area where the cells were square or polygonal, focal contact formation was not extensive or almost absent. In the peripheral area where single cells were scattered, focal contact formation was not extensive. The difference in the formation of focal contacts from the center part of the cultured cell sheet toward the, midperipheral area of the cell sheet was well correlated with that from the anterior portion of the lens toward the equator of the lens. Due to the extensive formation of focal contacts; in the midperipheral area, the cell sheet was used as an in vitro model to evaluate agents to modulate focal contacts.

Experiment 4: Resistance of Focal Contacts to Extracellular Calcium Depletion.

Materials and Method

Human lens epithelial cells cultured on glass coverslips were briefly washed twice with DPBS⁻ and exposed to 30 millimole/l (hereafter referred to as mM) EDTA in DPBS⁻ for 10 or 30 minutes at 37° C. The cells were then fixed with 3.7% paraformaldehyde and processed for observation of vinculin using immunofluorescence microscopy as described in Experiment 1.

Result

Some cells detached from the coverslips. Other cells remained adherent to the coverslips with strand-like structures bridging from the cell body. The fluorescence for vinculin was present on the terminal portion of the bridging structures on the coverslips. The localization of the fluorescent spots was typical for focal contacts. The result indicated that, despite the use of a higher concentration of EDTA solution (30 mM) and a long exposure (30 minutes), the attached cells remained attached to the coverslips with focal contacts. It was concluded that focal contacts were resistant to the cell separation induced by the extracellular calcium depletion.

EXAMPLE 1

Exposure of Plasminogen Solution to Cultured Human Lens Epithelial Cell

Material and Method

Cultured human lens epithelial cells prepared in Experiment 2 were briefly washed three times with an E-MEM and incubated in a solution of 10 μM Glu-plasminogen (American Diagnostica) in DPBS- for ten minutes at 37° C. The cells were then washed five times with an E-MEM. The cells were maintained in an E-MEM and observed under phase-contrast microscopy. Then evaluation was run in duplicate independently. The medium, in which the Glu-plasminogen was omitted and the concentrations of $Ca^{2+}$ and $Mg^{2+}$ were adjusted for physiological conditions, served as a control.

Result

In the mid-peripheral area where focal contacts were extensively formed, cells were separated or lysed. Some cells lost their nuclei. In contrast, cells in the center part of the cell sheet were not separated. Scattered single cells were partly separated. When the control medium was used instead of the Glu-plasminogen, almost all the cells remained attached after the 10-minutes exposure.

EXAMPLE 2

Human Lens Epithelial Cell Separation by Solution of Lys-plasminogen and EDTA

Materials and Method

Cultured human lens epithelial cells prepared in Experiment 2 were briefly washed three times with E-MEM and incubated in a solution of Lys-plasminogen (American Diagnostica) having a predetermined concentration and 30 mM EDTA in DPBS⁻ for four minutes at 37° C. The cells were then washed five times with E-MEM. The cells were then maintained in E-MEM and observed under phase-contrast microscopy. The media, in which the EDTA and Lys-plasminogen were omitted and the concentrations of $Ca^{2+}$ and $Mg^{2+}$ were adjusted for physiological condition, served as the controls. The evaluation was run in duplicate independently.

Result

The separation of the cells was summarized as follows:

Separation of cultured human lens epithelial cells

| Lys-plasminogen concentration | mean % cell separation |
| --- | --- |
| 12 μM | 85.1% (78.0–92.1%) |
| 18 μM | 99.8% (99.7–99.9%) |
| 24 μM | 99.9% (99.8–99.9%) |

With 12 μM of Lys-plasminogen and 30 mM EDTA, cells were completely separated in the center and the peripheral area of the cell sheet. In the midperipheral area of the cell sheet, however, cells remained partially attached to the substratum. With 113 μM or 24 μM of Lys-plasminogen and 30 mM EDTA, almost all the cells were separated,. When the control media were used, most of or almost all the cells remained attached to the substrata.

Accordingly, Lys-plasminogen was effective in epithelial cell separation, and especially, more than 99% of the lens epithelial cells were separated in four minutes when the cells were exposed to a solution of Lys-plasminogen and 30 mM EDTA in which Lys-plasminogen concentration was 18 μM or higher.

EXAMPLE 3

Human Lens Epithelial Cell Separation by a Reduced Volume of Solution of Lys-plasminogen and EDTA In Example 2, cultured human lens epithelial cells were exposed to 60 μl of a Lys-plasminogen and 30 mM EDTA solution. In this example, the volume of the solution was reduced to 4.5 μl. In order to reduce dilution effect caused by reduction of the volume of the treating solution, the area of cell growth on the culture dish was reduced to a 7 mm×7 rum square area by placing a square frame of PARAFILM® (AmericanNational Can) on the culture dish before experiments, followed by sterilization of the culture dish with the square frame. A 5.5 mm circular anterior capsule (23.7 mm²) having lens epithelial cells, was placed in the center of the 7 mm×7 mm square area and was allowed to grow for two weeks as in Example 2. In this chamber, approximately 1 to 2 μl of the medium remained after drainage of the medium. By using 4.5 μl of a 24 μM Lys-plasminogen and 30 mM EDTA solution, almost all of the cells were exfoliated in four minutes. Instead of the above solution, when a 18 μM Lys-plasminogen and 30 mM EDTA solution was used, the efficacy of the agent appeared to vary depending on the volume of the remaining medium. However, by performing sufficient drainage of the medium, almost all of the cells were exfoliated.

In this experiment, the population of the lens epithelial cells present in the 5.5 mm circular anterior capsule (23.7 mm²) was calculated at 28% of the entire lens epithelial cell population, based on the surface area. Thus, 4.5 μl of the solution in this experiment was equivalent to 16 µl (4.5 µl/28%) of the solution for the entire lens epithelial cells. As described earlier, in actual clinical application, introduction of 16 µl of a solution into the lens capsular bag will not cause an increase in pressure of the lens capsular bag to a level in which rupture of the lens capsule occurs.

EXAMPLE 4

Clinical Evaluation of Preferred Form of Operation

Human clinical trials are performed in cataract patients as follows: Extracapsular cataract extraction is performed with modifications. That is, after an incision is made in the anterior part of an eye, a solution of a mixture of an inhibitor and a viscoelastic material is introduced into the anterior chamber (examples of preferable compositions for clinical use will be described below). A small hole is then made in the anterior part of the lens capsule. A solution comprising of plasminogen and EDTA is introduced into the lens capsular bag through a fine cannula. Four minutes after the introduction of the solution of plasminogen and EDTA into the lens capsular bag, a solution of an inhibitor is introduced into the lens capsular bag. Following capsulotomy, emulsification or delivery of the lens nucleus is performed. The residual lens cortex is removed by using an irrigation and aspiration device. If applicable, an intraocular lens is inserted into the lens capsular bag as the prevailing extracapsular cataract extraction procedure. Postoperatively, development of posterior capsular opacification is evaluated by slitlamp examination as well as other routine postoperative examinations. As a result, very effective epithelial cell separation will be observed in the target area.

EXAMPLE 5

Clinical Evaluation of Preferred Form of Operation

In the procedure in Example 4, the step of introducing a solution of an inhibitor into the lens capsular bag is omitted. As a result, effective epithelial cell separation will be observed in the target area.

EXAMPLE 6

Clinical Evaluation of Preferred Form of Operation

In the procedure in Example 4, the step of introducing a solution of a mixture of am inhibitor and a viscoelastic material into the anterior chamber is omitted. As a result, effective epithelial cell separation will be observed in the target area Composition Example 1 for Clinical Use:

A treating composition to be introduced into the lens capsular bag comprises plasminogen and a chelating agent as follows:

12 µM Lys-plasminogen (American Diagnostica) and 30 mM EDTA 8 µl

An inhibiting composition to be introduced into the lens capsular bag comprises an inhibitor as follows:

1.1 mM Tranexamic acid (CYKLOKAPRON®, Kabi) 8 µl

An inhibiting composition to be introduced into the anterior chamber comprises a mixture of an inhibitor and a viscoelastic material as follows:

5.0 µM Tranexamic acid and sodium hyaluronate (Alcon Lab, Allergan Inc., Chiron Inc., Pharmacia & Upjohn Inc.)

Composition Example 2 for Clinical Use

A treating composition to be introduced into the lens capsular bag comprises plasminogen and a chelating agent as follows:

13.3 µM Lys-plasminogen and 30 mM EDTA 8 µl

An inhibiting composition to be introduced into the lens capsular bag comprises an inhibitor as follows:

1.2 mM Tranexamic acid 8 µl

An inhibiting composition to be introduced into the anterior chamber comprises a2 mixture of an inhibitor and a viscoelastic material as follows:

5.6 µM Tranexamic acid and sodium hyaluronate

Composition Example 3 for Clinical Use

A treating composition to be introduced into the lens capsular bag comprises plasminogen and a chelating agent as follows:

18 µM Lys-plasminogen and 30 mM EDTA 8 µl

An inhibiting composition to be introduced into the lens capsular bag comprises an inhibitor as follows:

1.6 mM Tranexamic acid 8 µl

An inhibiting composition to be introduced into the anterior chamber comprises a mixture of an inhibitor and a viscoelastic material as follows:

17 µM Tranexamic acid and sodium hyaluronate

Composition Example 4 for Clinical Use

A treating composition to be introduced into the lens capsular bag comprises plasminogen and a chelating agent as follows:

12 µM Lys-plasminogen and 30 mM EDTA 8 µl

An inhibiting composition to be introduced into the lens capsular bag comprises an inhibitor as follows:

1.1 mM Tranexamic acid 8 µl

Composition Example 5 for Clinical Use

A treating composition to be introduced into the lens capsular bag comprises plasminogen and a chelating agent as follows:

12 µM Lys-plasminogen and 30 mM EDTA 8 µl

An inhibiting composition to be introduced into the anterior chamber comprises a mixture of an inhibitor and a viscoelastic material as follows:

5.0 µM Tranexamic acid and sodium hyaluronate

Composition Example 6 for Clinical Use

A treating composition to be introduced into the lens capsular bag comprises plasminogen and a chelating agent as follows:

13.3 µM Lys-plasminogen and 30 mM EDTA 8 µl

An inhibiting composition to be introduced into the lens capsular bag comprises an inhibitor as follows:

1.2 mM Tranexamic acid 8 µl

An inhibiting composition to be introduced into the anterior chamber comprises a mixture of an inhibitor and a viscoelastic material as follows:

5.6 µM Tranexamic acid and chondroitin sulfate-sodium hyaluronate (Alcon Lab)

Composition Example 7 for Clinical Use

A treating composition to be introduced into the lens capsular bag comprises plasminogen and a chelating agent as follows:

13.3 µM Lys-plasminogen and 30 mM EDTA 8 µl

An inhibiting composition to be introduced into the lens capsular bag comprises am inhibitor as follows:

1.2 mM Tranexamic acid 8 µl

An inhibiting composition to be introduced into the anterior chamber comprises a mixture of an inhibitor and a viscoelastic material as follows:

5.6 µM Tranexamic acid and hydroxypropylmethyl cellulose (American Home Products)

Composition Example 8 for Clinical Use

A treating composition to be introduced into the lens capsular bag comprises plasminogen and a chelating agent as follows:

12 μM Lys-plasminogen and 30 mM EDTA 8 μl

An inhibiting composition to be introduced into the lens capsular bag comprises an inhibitor as follows:

2.2 mM p-aminomethyl benzoic acid 8 μl

An inhibiting composition to be introduced into the anterior chamber comprises a mixture of an inhibitor and a viscoelastic material as follows:

10 μM p-aminomethyl benzoic acid and sodium hyaluronate

Composition Example 9 for Clinical Use

A treating composition to be introduced into the lens capsular bag comprises plasminogen and a chelating agent as follows:

12 μM Lys-plasminogen and 30 mM EDTA 8 μl

An inhibiting composition to be introduced into the lens capsular bag comprises an inhibitor as follows:

7.7 mM 6-aminohexanoic acid (AMICAR®, Immunex Corp.) 8 μl

An inhibiting composition to be introduced into the anterior chamber comprises a mixture of an inhibitor and a viscoelastic material as follows:

35.0 μM 6-aminohexanoic acid and sodium hyaluronate

Composition Example 10 for Clinical Use

A treating composition to be introduced into the lens capsular bag comprises plasminogen and a chelating agent as follows:

12 μM Lys-plasminogen and 30 mM EDTA 8 μl

An inhibiting composition to be introduced into the lens capsular bag comprises an inhibitor as follows:

36 μM Aprotinin (TRASYLOL, Bayer Corp.) 8 μl

An inhibiting composition to be introduced into the anterior chamber comprises a mixture of an inhibitor and a viscoelastic material as follows:

5.0 μM Tranexamic acid and sodium hyaluronate

Composition Example 11 for Clinical Use

A treating composition to be introduced into the lens capsular bag comprises plasminogen and a chelating agent as follows:

12 μM Lys-plasminogen and 30 mM EDTA 8 μl

An inhibiting composition to be introduced into the lens capsular bag comprises an inhibitor as follows:

36 μM Aprotinin 8 μm

Composition Example 12 for Clinical Use

A treating composition to be introduced into the lens capsular bag comprises plasminogen as follows:

12 μM Lys-plasminogen 8 μl

An inhibiting composition to be introduced into the lens capsular bag comprises an inhibitor as follows:

36μM Aprotinin 8 μl

Other Composition Examples for Clinical Use

In Composition Examples 1–12, in place of Lys-plasminogen, Glu-plasminogen is used. $Val^{354}$-plasminogen, mini(-)plasminogen, or micro(-)plasminogen is also used in place of Lys-plasminogen or in combination with Lys-/Glu-plasminogen. When solely using $Val^{354}$-plasminogen, mini(-)plasminogen, or micro(-)plasminogen, its concentration is increased by approximately up to 10-fold. Further, in Composition Examples 1–9, in place of EDTA, EGTA is used at a concentrations of 4 mM.

Accordingly, the present invention provides extremely safe and effective compositions and methods to prevent the proliferation of remnant lens epithelial cells following cataract surgery. The compositions and the methods of the present invention require only a slight modification to the prevailing cataract surgical procedure as a step or steps of extracapsular cataract surgery. The modification is simple and not difficult for those skilled in the current cataract surgical procedure. Furthermore, the present invention can be applied in the procedures modified from the prevailing extracapsular cataract extraction. The modified procedures include possible future cataract surgery using laser energy.

It will be understood by those of skill in the art that numerous various modifications can be made without departing from the spirit of the present invention. Therefore, it should be clearly understood that the forms of the present invention are illustrative only and are not intended to limit the scope of the present invention.

Use of Combinations for Prevention of Posterior Capsular Opacification

Compositions and methods for prevention of posterior capsular opacification are the same as those set out in the above experiments and examples. These compositions and methods substantially successfully prevent posterior capsular opacification. However, there can be some surgically difficult cases and situations and challenging cases that may result in incomplete removal or separation of lens epithelial cells. The present invention provides improved methods for prevention of posterior capsular opacification to eliminate YAG laser capsulotomy.

In surgically difficult cases and situations and challenging cases, removal or separation of lens epithelial cells may become incomplete or insufficient to eliminate YAG laser capsulotomy. If air is accidentally introduced into an injection cannula or if a hole made in the lens capsule for introduction of an agent becomes too large,, insufficient or inappropriate introduction of an agent into the lens capsular bag or leaking of an agent from the lens capsular bag may occur. In addition, preexisting pathology of the lens capsule, e.g., damage caused by trauma, might not be recognized by surgeons prior to cataract surgery and may become a cause of leaking of an agent from the lens capsular bag, resulting in insufficient separation of lens epithelial cells. A surgeon who has just started to perform cataract surgery may be more likely o10 introduce an agent in an unintended manner or site.

Indeed, there may be some cases in which incomplete removal or separation of lens epithelial cells may occur due to still unknown reasons or unexpected clinical situations.

In a pediatric eye, the lens volume is small and only a smaller volume of solution can be confined in the lens capsular bag as compared to the adult counterpart. However, the proliferative capacity of lens epithelial cells in a pediatric eye is much stronger than that in the elders (Hiles et al., J Cataract Refract Surg. 13:493–497,1987.). Therefore, prevention of posterior capsular opacification in a pediatric eye is quite challenging. Even in pediatric cases, elimination of YAG laser capsulotomy can be achieved by using the present invention without increasing the concentration of the agent to be used and/or the time required for the treatment.

What were found in the present invention to achieve elimination of YAG laser capsulotomy in the surgically difficult cases and situations and the challenging cases are improved methods which comprise inserting an ocular implant that has a property lo reduce the development of posterior capsular opacification and introducing an agent into the lens capsular bag.

It was unexpectedly found that YAG laser capsulotomy is eliminated by the use of an agent alone or the synergistic effect with implantation of an ocular implant that has a property to reduce the development of posterior capsular opacification. Therefore, the present invention has advantages over the prior art that the possibility to eliminate YAG laser capsulotomy is maximized and elimination of the YAG laser capsulotomy is accomplished even when lens epithelial cells are insufficiently removed or separated. To secure the elimination of YAG laser capsulotomy, the improved methods may be performed in any patient with cataract.

Any agent having a property to prevent posterior capsular opacification can b[]e used for this purpose. The agent may be toxic to lens epithelial cells or has a property lo separate or kill lens epithelial cells or to inhibit proliferation of lens epithelial cells. Preferably the agent is a treating solution having a property or properties to separate lens epithelial cells.

The treating solution that is more preferable to be used comprises a proenzyme or a focal contact-modulating substance as disclosed hereinabove. The treating solution may be prepared in a physiologically acceptable solution, which includes, but is not limited to, saline, phosphate-buffered saline, or the like. Among proenzymes, a proenzyme of a serine protease is preferably to be used. It should be appreciated that tie damage to the lens capsule and the zonules is avoided by the use of a proenzyme. Plasminogen is more preferable to be used for the proenzyme or the focal contact-modulating substance. Particularly, Lys-plasminogen is suited to be used because plasmin can be generated rapidly and is favorable to be applied to the prevailing cataract surgery in which the entire procedure is completed in thirty minutes in most cases. The treating solution may further include ethylenediamine tetraacetic acid (EDTA) to secure the passage of the treating solution into the interface between lens epithelial cells and the lens capsule and separate lens epithelial cells in the anterior portion of the lens. In the present invention, an ocular implant is inserted into the lens capsular bag. The term "ocular implant" implies an IOL or a capsular ring. The term -"capsular ring" implies an artificial device to be inserted into the lens capsular bag, which includes, but is not limited to, capsular tension ring, capsule-bending ring, capsular edge ring (Morcher GmbH, Germany), endocapsular tension ring, equator ring, polymer implant (U.S. Pat. No. 5,618,553 to Kelleher 1997), device for stretching the crystalline capsule, capsular bag implants (U.S. Pat. No. 5,593,436 to Langerman 1997) or the like.

Preferably, an IOL is used for the ocular implant. Posterior chamber IOLs are suited to be used for the IOL. Biconvex IOLs with truncated sharp posterior optic edges,,, convex-plano (plano-posterior) IOLs, and concave-posterior IOLs are suited to be used for the posterior chamber IOL. The term "posterior optic edge" of an IOL implies an optic edge that is formed with posterior surface of the optic. Anterior optic edge of a biconvex IOL to be used may be smooth or sharply truncated. The term "concave-posterior IOL" implies an IOL in which posterior surface of the optic is at least partly concave. An IOL to be used may have a ridge or a protrusion on the optic. The optic material of an IOL to be used may be any material acceptable for clinical use. The materials for an IOL to be used includes, but are not limited to, silicone, hydrogel, acrylic polymer and a combination of two or more of this group. "Acrylic polymer" includes the preferred polyalkylacrylates, such as PMMA, as well as copolymers of two or more acrylic monomers such as methylmethacrylate and buthylmethacrylate. IOLs to be used include, but is not limited to, AcrySof® IOL (Alcon Lab.), CeeOn® 911 silicone IOL (Pharmacia & Upjohn Inc.), and a biconvex IOL of which the optic is modified to have truncated sharp posterior edge. The IOLs to be modified far application in the present invention include SoFlex® (Bausch & Lomb Surgical), Chiroflex® (Bausch & Lomb Surgical), Elastimide (Staar Surgical), MemoryLens, (Ciba Vision Ophthalmics), EasAcryl®1 (Bausch & Lomb Surgical), Sensar® (Allergan Inc.) and polymethylmethacrylate (PMMA) IOLs. Preferably, a foldable ICL is used for the posterior chamber IOL because a foldable IOL can be inserted into the eye through a small incision and astigmatism occurring following surgery can be minimized. The term "a foldable IOL" means an IOL that can be folded for insertion of the IOL into the eye. Haptics of a posterior chamber IOL to be used are preferably forwardly angulated from the IOL optic, because when a posterior chamber IOL with forwardly angulated haptics is inserted into the lens capsular bag, the optic can be pressed against the posterior capsule. The posterior optic edge of the IOL, working as a barrier, can reduce migration and/or proliferation of lens epithelial cells toward the center part of the posterior capsule and the development of posterior capsular opacification can be reduced. The details about the mechanism is described later.

In the prevailing cataract surgery, when capsulotomy is performed and the anterior capsular rim is made sufficiently smooth without irregular capsular flaps and sufficiently small, e.g., by using continuous circular capsulorhexis, the likelihood of developing adhesion between the anterior capsule and the posterior capsule is reduced and the development of posterior capsular opacification can be delayed or reduced. The term "capsulotomy" implies herein a procedure to make an opening in the lens capsule. The term "capsulorhexis" implies a technique to tear the lens capsule, which is also called continuous circular capsulorhexis or continuous curvillinear capsulorhexis. In the condition, anterior capsular rim constricts without causing tears postoperatively. The anterior capsule is strongly resistant to a force induced by haptics of a posterior chamber IOL that is inserted into the lens capsular bag. The IOL optic is pushed posteriorly against the posterior capsule, especially when an IOL with forwardly angulated haptics is inserted. The posterior optic edge, having a contact with the residual posterior capsule, working as a barrier, can reduce proliferation and/or migration of lens epithelial cells toward the center part of the posterior capsule to reduce the likelihood of the occurrence of visual disturbance. Bending of the posterior capsule may be caused by the posterior optic edge of the IOL. In accordance with this theory, development of posterior capsular opacification can be reduced by implantation of plano-convex IOLs (Yamada et al.,1995. Nagata et al., 1996.) and AcrySof® IOLs (Oshika et al., 1998). To avoid damage to surrounding eye tissues such as the iris and the corneal endothelium, an inhibitor may be used. An inhibitor may be introduced as a mixture with a viscoelastic material into the anterior chamber and/or introduced into the lens capsular bag as a solution of an inhibitor. Preferably, an ω-amino acid is used far the inhibitor.

When the present invention is practiced in cataract surgery, an incision is made in the anterior part of the eye. Then a hole or an opening is made in the lens capsule and a treating solution is introduced into the lens capsular bag. The term "lens capsular bag" implies the lens in which a hole or an opening is made. Adhesion between lens epithelial cells and the lens capsule is so strong that the interface between lens epithelial cells and the lens fibers, not the interface between the lens capsule and lens epithelial cells, is separated by the introduction of the solution. A mixture of a viscoelastic material and an inhibitor is preferably introduced into the anterior chamber prior to make a hole or an opening in the lens capsule. After a treating solution is allowed to separate lens epithelial cells from the lens capsule, a solution of an inhibitor is preferably introduced into the lens capsular bag. Then capsulotomy, preferably capsulorhexis, is performed and the lens nucleus is removed by any procedure which includes phacoemulsification, simple delivery of the nucleus through the incision in the anterior part of the eye, and the removal using laser energy. The remaining lens fibers are completely removed by using an aspiration and irrigation device while the anterior chamber and the lens capsular bag are irrigated with a physiological solution. Then an ocular implant is inserted into the remaining lens capsular bag. The term "remaining lens capsular bag" implies the lens capsular bag after capsulorhexis or capsulotomy is performed. Preferably, a viscoelastic material is introduced into the anterior chamber and the lens capsular bag prior to IOL insertion. Then the incision in the anterior part of the eye is closed. The introduced viscoelastic material is washed out by irrigating solution before the incision is closed. Alternatively, a treating solution may be introduced into the lens capsular bag after the lens nucleus is removed. The proposed surgical procedures are not difficult for those who are skilled in the prevailing cataract surgery.

It will be understood by those of skill in the art that numerous various modifications can be made without departing from the spirit of the present invention. Therefore, it should be clearly understood that the forms of the present invention are illustrative only and are not intended to limit the scope of the present invention.

What is claimed is:

1. A method for preventing posterior capsular opacification comprising:

making an incision in the anterior part of the eye;

making a hole or an opening in the lens capsule;

introducing a treating solution into the lens capsular bag, wherein said treating solution comprises a focal contact-modulating substance and a carrier;

inserting an ocular implant inside the remaining lens capsular bag, wherein said ocular implant has a property to reduce the development of posterior capsular opacification; and closing the incision in the anterior part of the eye.

2. The method according to claim 1, wherein said ocular implant is a posterior chamber intraocular lens or a capsular ring.

3. The method according to claim 2, wherein said posterior chamber intraocular lens is selected from the group consisting of biconvex intraocular lens with truncated sharp posterior optic edge, convex-piano (plano-posterior) intraocular lens amid concave-posterior intraocular lens.

4. The method according to claim 2, wherein said posterior chamber intraocular lens is a foldable intraocular lens.

5. The method according to claim 2, wherein said posterior chamber intraocular lens has forwardly angulated haptics.

6. The method according to claim 1, wherein said focal contact-modulating substance is a proenzyme.

7. The method according to claim 6, wherein said proenzyme comprises a proenzyme of a serine protease.

8. The method according to claim 7, wherein said proenzyme of a serine protease is plasminogen.

9. The method according to claim 8, wherein said plasminogen is Lys-plasminogen.

10. The method according to claim 1 further comprises introducing a mixture of a viscoelastic material and an inhibitor into the anterior chamber prior to making hie hole or the opening in the lens capsule.

11. The method according to claim 1 further comprising introducing an inhibitor into the lens capsular bag after introducing said treating solution into the lens capsular bag.

12. The method according to claim 1, wherein said treating solution further comprises a calcium chelating agent or a salt thereof.

13. The method according to claim 12, wherein said calcium chelating agent is ethylenediamine tetraacetic acid (EDTA).

14. The method according to claim 1, wherein said treating solution further comprises a dye.

15. A method for preventing posterior capsular opacification comprising:

making an incision in the anterior part of the eye;

making a hole or an opening in the lens capsule;

introducing a treating solution into the lens capsular bag, wherein said treating solution comprises a proenzyme and a carrier;

inserting an ocular implant inside the remaining lens capsular bag, wherein said ocular implant has a property to reduce the development of posterior capsular opacification; and closing the incision in the anterior part of the eye.

16. The method according to claim 15, wherein said ocular implant is a posterior chamber intraocular lens or a capsular ring.

17. The method according to claim 16, wherein said posterior chamber intraocular lens is selected from the group consisting of biconvex intraocular lens with truncated sharp posterior optic edge, convex-plano (plano-posterior) intraocular lens aid concave-posterior intraocular lens.

18. The method according to claim 16, wherein said posterior chamber intraocular lens is a foldable intraocular lens.

19. The method according to claim 16, wherein said posterior chamber intraocular lens has forwardly angulated haptics.

20. The method according to claim 15 further comprising introducing a mixture of a viscoelastic material and an inhibitor into the anterior chamber prior to making the hole or the opening in the lens capsule.

21. The method according to claim 15 further comprising introducing an inhibitor into the lens capsular bag after introducing said treating solution into the lens capsular bag.

22. The method according to claim 10 or 11, wherein said inhibitor is an $\omega$-amino acid.

* * * * *

UNITED STATES PATENT AND TRADEMARK OFFICE
CERTIFICATE OF CORRECTION

PATENT NO.    : 6,186,148 B1
DATED         : February 13, 2001
INVENTOR(S)   : Kiyoshi Okada It is certified that error appears in the above-identified patent and that said Letters Patent is hereby corrected as shown below:

<u>Claim 3,</u>
Please change "convex-piano" to -- convex-plano --

<u>Claim 10,</u>
Please change "making hie hole" to -- making the hole --

Signed and Sealed this

Nineteenth Day of March, 2002

Attest:

JAMES E. ROGAN
*Attesting Officer*  *Director of the United States Patent and Trademark Office*